(12) United States Patent
Barker et al.

(10) Patent No.: US 10,653,855 B2
(45) Date of Patent: May 19, 2020

(54) RESPIRATORY ASSISTANCE APPARATUS

(71) Applicant: Fisher & Paykel Healthcare Limited, Auckland (NZ)

(72) Inventors: Dean Antony Barker, Auckland (NZ); Russel William Burgess, Auckland (NZ); Peter Geoffrey Hawkins, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 225 days.

(21) Appl. No.: 14/764,358

(22) PCT Filed: Jan. 30, 2014

(86) PCT No.: PCT/NZ2014/000010
§ 371 (c)(1),
(2) Date: Jul. 29, 2015

(87) PCT Pub. No.: WO2014/120024
PCT Pub. Date: Aug. 7, 2014

(65) Prior Publication Data
US 2015/0359990 A1 Dec. 17, 2015

Related U.S. Application Data

(60) Provisional application No. 61/758,663, filed on Jan. 30, 2013.

(51) Int. Cl.
*A61M 16/10* (2006.01)
*A61M 16/16* (2006.01)
(Continued)

(52) U.S. Cl.
CPC ........... *A61M 16/1075* (2013.01); *A61L 2/07* (2013.01); *A61M 16/0051* (2013.01);
(Continued)

(58) Field of Classification Search
CPC .................. A61M 16/1075; A61M 16/161
(Continued)

(56) References Cited

U.S. PATENT DOCUMENTS

| 3,873,806 A | 3/1975 | Schossow |
| 4,013,742 A | 3/1977 | Lang |

(Continued)

FOREIGN PATENT DOCUMENTS

| FR | 2390170 | 12/1978 |
| GB | 1581905 | 12/1980 |

(Continued)

OTHER PUBLICATIONS

International Search Report; PCT/NZ2014/000010; dated Jun. 23, 2014; 6 pages.

*Primary Examiner* — Kevin Joyner
(74) *Attorney, Agent, or Firm* — Knobbe, Martens, Olson & Bear, LLP

(57) ABSTRACT

A respiratory assistance apparatus (4) is provided, adapted to deliver gases to a user or patient (1). The apparatus (4) comprises a housing (10) provided with a chamber (5) and a heater (25), the chamber (5) comprising at least one gas port (15) connected to, or arranged to be connected to, at least one intermediate passageway (12). The apparatus (4) is operative according to a disinfection mode of predetermined profile in which the heater (25) heats liquid in the chamber (5) to produce vapour at or above a target dewpoint temperature and/or humidity level. The apparatus (4) is arranged such that the vapour is delivered to the intermediate passageway (12) to disinfect the intermediate passageway (12) with moist heat throughout a predetermined duration of the disinfection mode. Associated attachments and methods are also provided.

26 Claims, 18 Drawing Sheets

(51) Int. Cl.
*A61L 2/07* (2006.01)
*A61M 16/00* (2006.01)
*A61M 39/20* (2006.01)

(52) U.S. Cl.
CPC ...... *A61M 16/0069* (2014.02); *A61M 16/024* (2017.08); *A61M 16/109* (2014.02); *A61M 16/1095* (2014.02); *A61M 16/16* (2013.01); *A61M 39/20* (2013.01); *A61M 16/107* (2014.02); *A61M 16/1055* (2013.01); *A61M 2016/0039* (2013.01); *A61M 2205/3368* (2013.01)

(58) Field of Classification Search
USPC .................................................. 128/204.17
See application file for complete search history.

(56) References Cited

U.S. PATENT DOCUMENTS

| | | | |
|---|---|---|---|
| 4,089,915 A | 5/1978 | Jackson | |
| 4,110,419 A | 8/1978 | Miller | |
| 4,224,939 A | 9/1980 | Lang | |
| 5,372,753 A | 12/1994 | Morton | |
| 7,182,321 B2 | 2/2007 | Huang et al. | |
| 2002/0078733 A1 | 6/2002 | Seakins et al. | |
| 2004/0231668 A1 | 11/2004 | Kates | |
| 2005/0268910 A1 | 12/2005 | Nord et al. | |
| 2006/0251540 A1* | 11/2006 | Benning | A61L 2/07 422/3 |
| 2008/0054497 A1 | 3/2008 | Bradley et al. | |
| 2008/0310994 A1 | 12/2008 | O'Donnell et al. | |
| 2010/0282247 A1 | 11/2010 | Kadrichu et al. | |
| 2011/0180068 A1* | 7/2011 | Kenyon | A61M 16/00 128/203.26 |
| 2012/0157794 A1 | 6/2012 | Zhang et al. | |

FOREIGN PATENT DOCUMENTS

| | | |
|---|---|---|
| JP | 2001-321443 A | 11/2001 |
| SU | 1209215 A | 2/1986 |
| WO | WO 2009/015410 A1 | 2/2009 |
| WO | WO 2012/100291 A1 | 8/2012 |
| WO | WO 2013/151443 | 10/2013 |

* cited by examiner

RESPIRATORY ASSISTANCE APPARATUS

CROSS-REFERENCE TO RELATED APPLICATIONS

This application claims priority from U.S. Provisional Application No. 61/758,663, filed on 30 Jan. 2013, the contents of which are incorporated herein by reference.

BACKGROUND OF THE INVENTION

Field of the Invention

This invention relates to a respiratory assistance apparatus adapted to deliver respiratory gases to a user or patient. More particularly, the invention relates to a respiratory assistance apparatus provided with a disinfection mode and a method of disinfecting a respiratory assistance apparatus using a disinfection mode.

Description of the Related Art

A respiratory assistance apparatus typically comprises a humidifier, a gases inlet to supply a gases flow from a gases source to the humidifier, and a patient outlet to deliver a gases flow from the humidifier to the user or patient. The gases source can be a blower, fan, pressurised tank, compressor, or the like. An inspiratory tube can be connected between the patient outlet and a patient interface that is arranged to be mounted at or on the face of the user or patient. The patient interface may comprise a full face mask, nasal mask, nasal cannula, oral mouthpiece, or tracheostomy fitting.

One form of respiratory assistance apparatus can comprise an integrated system, where the gases source and the humidifier are contained within the same housing. With an integrated system, the patient outlet is typically mounted on the housing, and the humidifier and the patient outlet are typically connected via an intermediate passageway located at least partially within the housing.

Such respiratory assistance apparatus may be used in hospitals, other healthcare organisations, and care homes for example. They may also be used at the home of a user or patient. It is a problem in any such environment to keep a respiratory assistance apparatus clean and free from potentially harmful bacteria. It is often desirable that at least some components of the apparatus can be reused with subsequent users or patients, rather than requiring a new apparatus for each user or patient. In such circumstances, it is important that the apparatus can be cleaned to a sufficiently high standard for safe reuse. In particular, it may be required that some components of the apparatus can be disinfected, even if other components, such as the inspiratory tube and the patient interface, are to be replaced.

It is not usually required to disinfect components that are in the gases flow path up to the chamber inlet, because the gases that contact such components are typically relatively dry external air or oxygen. However, it is often necessary to clean the components in the subsequent gases flow path that are subjected to moisture, because moisture is susceptible to carrying bacteria which can cause the establishment and growth of biofilms that can be transmitted to the patient. Whilst some components are accessible and therefore can be relatively easily cleaned (e.g., some patient interfaces may be placed in a dishwasher), other components are contained within the housing, or may have internal features that are difficult to access, and thus are not easily cleaned. One example of such a component is the aforementioned intermediate passageway that links the humidifier to the patient outlet. In some cases, components cannot easily be removed from the apparatus for cleaning, or at least not without specialist or relatively skilled personnel. Removal of components also introduces a risk of damage to the components or the apparatus, or of incorrect refitting of the components after cleaning.

SUMMARY OF THE INVENTION

It is therefore an object of the invention to provide a respiratory assistance apparatus, and a method of disinfecting a respiratory assistance apparatus, which overcomes or at least ameliorates one or more of the disadvantages of the prior art, or alternatively at least provides the public or industry with a useful choice.

Further objects of the invention will become apparent from the following description.

Accordingly, in one aspect the invention may broadly be said to consist in a respiratory assistance apparatus adapted to deliver a gases flow to a user or patient, comprising a housing provided with a chamber and a heater, the chamber comprising at least one chamber port connected to, or arranged to be connected to, at least one intermediate passageway, the apparatus being operative according to a disinfection mode of predetermined profile in which the heater heats a liquid in the chamber to produce vapour or steam at or above a setpoint temperature, namely a target dewpoint temperature, the apparatus being arranged such that the vapour is delivered to the intermediate passageway to disinfect the intermediate passageway with moist heat, the vapour at or above the target dewpoint temperature continuing to be delivered to the intermediate passageway throughout the predetermined duration of the disinfection mode.

The predetermined profile may include a combination of some or all of duration, temperature, moisture and pressure.

The at least one chamber port may comprise a chamber inlet port and a chamber outlet port, the chamber inlet port being arranged to be in fluid communication in use with a gases source in the housing. The gases source may comprise a blower, fan or compressor arranged to deliver a gases flow through the chamber inlet port and into the chamber. Such arrangements are not essential due to the expansion of the heated water but are preferred to prevent steam being delivered to other components of the apparatus via the chamber inlet port. Such components may be susceptible to damage if subjected to steam or chemical vapours from disinfection. Alternatively, a valve could be used to prevent an undesirable flow of vapour, directing such flow of vapour through the chamber outlet port.

In one example, the chamber comprises part of a humidifier of the apparatus, the humidifier being arranged to humidify the gases flow prior to delivery of the gases flow to the user or patient when the apparatus is operating in a non-disinfection mode. In this example, the liquid used during the disinfection mode may be a liquid normally used for humidification purposes. One example of a suitable humidification liquid is water.

In another example, the chamber comprises a disinfection chamber. In this example, the liquid used during the disinfection mode may be a disinfecting and/or sterilising liquid. One example of a suitable disinfecting and/or sterilising liquid is a mixture of water and a disinfecting and/or sterilising chemical. The disinfection chamber may be provided with a liquid injection port to enable disinfecting and/or sterilising liquid to be injected into the chamber.

Alternatively, the disinfection chamber may be sealed, having been pre-charged with disinfecting and/or sterilising liquid prior to use in the disinfection mode.

The chamber may be removably mounted on the apparatus. The chamber may be reusable or disposable.

The chamber may comprise an identifier, the apparatus being operative to detect the identifier and thus the presence of the chamber. The identifier may comprise a chamber inlet port arranged to have a high flow resistance which can be detected by the apparatus to identify the presence of the chamber. The high flow resistance also prevents vapour undesirably passing through the chamber inlet port into the housing, by causing local high flow velocity at the chamber inlet port when a gases flow is delivered through the chamber inlet port from the housing.

The intermediate passageway may comprise an internal passageway located at least partially within the housing. The intermediate passageway may comprise a conduit or elbow.

The intermediate passageway preferably directly or indirectly connects a gases inlet that allows a gases flow into the housing with a patient outlet that delivers a gases flow to the user or patient.

One end of the intermediate passageway may comprise the patient outlet.

In one example, during the disinfection mode, the end of the intermediate passageway comprising the patient outlet is connected to the chamber outlet port via a removable disinfection tube which delivers vapour or steam to the intermediate passageway. The disinfection tube may be heated. In this example, the at least one port of the chamber is connected to the at least one intermediate passageway, by way of a temporary connection, that is, a connection used specifically for cleaning or disinfection.

In another example, the chamber outlet port is directly connected to the intermediate passageway at an opposed end from the patient outlet. In this example, the at least one port of the chamber is connected to the at least one intermediate passageway by way of a permanent connection, that is, a connection that remains after termination of the disinfection mode.

The intermediate passageway may comprise an elbow having opposed ends linked by an intermediate bent portion. In one example, the bent portion is bent through 90°.

The intermediate passageway may be provided with at least one sensor operative to generate a signal indicative of, for example, flow rate, moisture content or temperature at or proximate to the intermediate passageway.

A cap may be provided comprising an engaging formation arranged to engage with one end of the intermediate passageway to mount the cap on said end, the cap comprising a flow restrictor arranged to restrict flow of fluid through the intermediate passageway when the cap is so mounted, to provide back pressure in the intermediate passageway during the disinfection mode. Additionally or alternatively, the cap may comprise an antibacterial filter. The cap may comprise an identifier. Non-limiting examples of a suitable identifier include a magnet, an RFID tag, or a source of electrical resistance such as a resistor.

The apparatus may be operative to heat the liquid to produce vapour at or above a target dewpoint temperature, that is, a fixed dewpoint temperature determined prior to initiation of the disinfection mode. Preferably, the target dewpoint temperature is a minimum dewpoint temperature required for effective disinfection by moist heat.

The apparatus may be operative to heat the liquid to produce vapour at or above a dewpoint temperature selected by a clinician or user, that is, a variable dewpoint temperature determined before or after initiation of the disinfection mode.

The target dewpoint temperature may be greater than 70° C., is preferably greater than 80° C., and is most preferably greater than 90° C. In some configurations, the target dewpoint temperature may be less than 110° C., or less than 105° C., or less than 95° C. The presence of moist heat in the gases flow enables the target dewpoint temperature to be substantially reduced as compared to target temperatures of prior methods using dry or non-humidified air.

Note, in this and other aspects of the invention, that the target dewpoint temperature may be set and measured within the chamber (e.g., at the chamber outlet port) and/or within the intermediate passageway and/or subsequent thereto. The target dewpoint temperature may require adjustment depending on where it is measured to ensure adequate disinfection efficacy.

Further, the target dewpoint temperature may be defined by a dewpoint temperature range.

Yet further, the target dewpoint temperature may be varied within the disinfection cycle. For example, in one example disinfection cycle, the target dewpoint temperature may generally be relatively low, say around 70° C., and increased for a short portion of the cycle to say 90° C., potentially reducing the time required for disinfection and/or better ensuring adequate disinfection efficacy.

The apparatus may be operative to control the duration of the disinfection mode in dependence upon the target and/or a measured dewpoint temperature. The apparatus may be operative to control the duration of the disinfection mode by reference to a lookup table, an algorithm or a formula relating the duration of the disinfection mode to a range of target and/or measured dewpoint temperatures. The lookup table can relate the duration of the disinfection mode to a range of target and/or measured dewpoint temperatures. The apparatus may be operative to control the target and/or measured dewpoint temperature by reference to at least one of a lookup table, an algorithm, and a formula relating the target and/or measured dewpoint temperature to a duration of the disinfection mode.

In addition to reducing the temperature required for disinfection, the use of vapour in the gases flow can also reduce the length of time required for disinfection. For example, 15 to 45 minutes may suffice, preferably around 30 minutes. In some configurations, the duration is less than 60 minutes or less than 50 minutes.

Preferably, the apparatus comprises a chamber sensor operative to generate a signal indicative of whether the chamber is mounted on the apparatus. The chamber sensor may be operative to generate a signal indicative of whether a specific chamber is mounted on the apparatus. The chamber sensor may comprise the combination of a pressure/flow sensor and a flow restriction on the specific chamber, the flow restriction restricting gases flow through the chamber which can be detected by the pressure/flow sensor.

Preferably, the apparatus comprises a patient interface sensor operative to generate a signal indicative of whether a patient interface is connected to the apparatus, and to activate the disinfection mode only when the signal indicates that a patient interface is not connected to the apparatus. The patient interface sensor may be operative to detect the presence of a cap or other attachment used in disinfection on one end of the intermediate passageway, and to generate the signal indicative that a patient interface is connected to the apparatus, when no cap or other disinfection mode attachment is detected.

Preferably, the apparatus comprises a disinfection mode sensor operative to generate a disinfection mode activation signal. The disinfection mode sensor may be operative to generate the disinfection mode activation signal by detecting at least one of: a cap or other disinfection mode attachment being mounted on one end of the intermediate passageway; the chamber being mounted on the housing; and/or a clinician or user input.

The apparatus may comprise a chamber liquid level detector operative to generate a signal indicative of the liquid level in the chamber. The apparatus may be operative, in dependence upon the liquid level signal detected, to vary at least one of: the flow rate of the gases flow exiting the chamber; the target dewpoint temperature of the vapour; and/or the duration of the disinfection mode.

A liquid level detector may additionally or alternatively be used to detect whether the chamber includes a sufficient level of liquid to complete a disinfection process. This may be a predetermined, fixed level or an adaptable level based on the parameters of the process being used. An alarm or indicator light or display may alert a user to an insufficient level of liquid. Disinfection mode may be inhibited until sufficient liquid is present in the chamber, or a notification may be generated indicating that disinfection has not completed.

Preferably, the required level of liquid is determined prior to initiation of disinfection to optimize the disinfection mode. Note, however, that rather than having to repeat disinfection in the event of a shortage of liquid, the target dewpoint temperature and/or the duration of the disinfection process may simply be increased, with these being closer to parameters used in prior art arrangements that do not include the use of moist heat.

Additionally or alternatively, the chamber may be provided with a visible mark whereby a user fills the chamber to or above that mark prior to disinfection.

Additionally or alternatively, a chamber that is specifically used for disinfection may be pre-charged or filled with a predetermined amount of liquid that has been determined to be sufficient to provide the required disinfection efficacy.

Depending on the liquid used, there may be an additional purging or rinsing step after disinfecting to remove or neutralise said liquid.

The apparatus may include a drying mode that is initiated subsequent to the disinfection mode, wherein the intermediate passageway and/or other components are dried. This may be achieved using heat generated by the heater when all of the liquid has been completely used, or via a separate heater element, or by increasing the gases flow rate through the intermediate passageway, for example. The duration of the drying mode may be predetermined, clinician or user controlled, or controlled in dependence on moisture levels detected in the intermediate passageway.

According to a second aspect, the invention may broadly be said to consist in a cap for use with a respiratory assistance apparatus according to the first aspect of the invention, the cap comprising an engaging formation or engaging portion arranged to engage with and/or fluidly couple to one end of the intermediate passageway of the respiratory assistance apparatus to mount the cap on said end, the cap comprising at least one of a flow restrictor arranged to restrict flow of liquid through the intermediate passageway when the cap is so mounted to provide back pressure in the intermediate passageway during the disinfection mode; and a filter.

The flow restrictor may comprise a filter. The filter may be an anti-bacterial filter. The filter may be arranged to prevent leakage of liquid through or around the filter. The geometry of the cap may be arranged to prevent liquid contacting the filter.

The flow restrictor may comprise an orifice.

The cap may comprise a temperature sensor operative to generate a signal indicative of the temperature of the gases flow at or proximate to the cap.

The cap may comprise an identifier. Non-limiting examples of a suitable identifier include a magnet, an RFID tag, or a source of electrical resistance such as a resistor. The identifier may simply identify the type of device (i.e., the cap as opposed to other items that may be connected thereto). This may be used by the apparatus to switch to a disinfection mode on detection of the cap and/or to generate an error message to a user that the apparatus is not correctly configured if a disinfection mode is otherwise selected and the cap is not detected.

The cap may comprise an open-ended cavity which defines a volume suitable for measuring an amount of a liquid for use in the apparatus in the disinfection mode.

According to a third aspect, the invention may broadly be said to consist in a method of disinfecting a respiratory assistance apparatus adapted to deliver a gases flow to a user or patient, according to a disinfecting mode, the apparatus comprising a chamber provided with a port in fluid communication with an intermediate passageway, the method comprising the steps of: heating a liquid in the chamber to produce vapour or steam at or above a target dewpoint temperature; delivering the vapour through the port to the intermediate passageway; and continuing to deliver vapour at or above the target dewpoint temperature through the port to the intermediate passageway throughout a predetermined duration of the disinfection mode.

The target dewpoint temperature may be predetermined, that is, fixed prior to initiation of the disinfection mode, or selected by a user, or determined based on other detected parameters.

The method may include a step, prior to the heating step, of setting or selecting the target dewpoint temperature before or after initiation of the disinfection mode.

The target dewpoint temperature may be greater than 70° C., is preferably greater than 80° C., and is most preferably greater than 90° C.

The method may include an additional step of controlling the duration of the disinfection mode in dependence upon the target and/or a measured dewpoint temperature. The method may include an additional step of referencing a lookup table using an algorithm or a formula relating the duration of the disinfection mode to a range of target and/or measured dewpoint temperatures.

The method may include an additional step of drying the intermediate passageway, after delivering the vapour for the predetermined duration.

As with previous and further aspects, the liquid may be water, a disinfecting and/or sterilising chemical, and/or a mixture thereof. Where a chemical or chemicals are used, an additional step of purging or rising the apparatus may be performed whereby water or a neutralising chemical is flushed therethrough.

According to a fourth aspect, the invention may broadly be said to consist in a respiratory assistance apparatus adapted to deliver a gases flow to a user or patient, comprising a housing provided with a chamber and a heater, the chamber comprising at least one port connected to, or arranged to be connected to, at least one intermediate passageway, the apparatus being operative according to a disinfection mode of predetermined profile in which the heater heats liquid in the chamber to produce vapour or steam at or above a target dewpoint temperature, the apparatus being arranged such that the vapour is delivered to the intermediate passageway to disinfect the intermediate passageway with moist heat, the apparatus further comprising a cap arranged to be mounted at one end of the intermediate passageway, the cap being provided with a flow restriction arranged to provide a back pressure in the intermediate passageway during the disinfection mode.

The heater may subsequently be used, once all liquid in the chamber has been completely used, to heat the gases flow within the apparatus to dry the intermediate passageway.

According to a fifth aspect, the invention may broadly be said to consist in a respiratory assistance apparatus adapted to deliver a gases flow to a user or patient, comprising a housing having a patient outlet, a chamber, and an intermediate gases flow path between the patient outlet and the chamber, the apparatus being operative during a disinfection mode of predetermined profile, to heat the liquid to generate and deliver vapour or steam at or above a target dewpoint temperature from the chamber to the intermediate gases flow path to disinfect the intermediate gases flow path with moist heat throughout the predetermined duration of the disinfection mode.

According to a sixth aspect, the invention may broadly be said to consist in a method of disinfecting a respiratory assistance apparatus adapted to deliver a gases flow to a user or patient according to a disinfecting mode comprising the steps of: connecting a chamber to the apparatus; heating liquid in the chamber to produce vapour or steam at or above a target dewpoint temperature; and delivering the vapour portion of the liquid to a component of the apparatus to disinfect that component with moist heat.

According to a seventh aspect, the invention may broadly be said to consist in a respiratory assistance apparatus adapted to deliver a gases flow to a patient, comprising a housing having a gases inlet and a patient outlet, the gases inlet being in communication with the patient outlet via an intermediate passageway, the apparatus further comprising a humidifier arranged between the gases inlet and the patient outlet and comprising a chamber and heater arranged, in a respiratory assistance mode, to humidify the gases flow prior to delivery of the gases flow to the patient outlet, the apparatus also being arranged, according to a disinfection mode of predetermined profile, to control the heater to heat the liquid in the chamber to produce vapour or steam at or above a target dewpoint temperature, and to deliver the vapour to the intermediate passageway to disinfect the intermediate passageway with moist heat throughout the predetermined duration of the disinfection mode.

According to an eighth aspect, the invention may broadly be said to consist in a respiratory assistance apparatus adapted to deliver a gases flow to a user or patient, comprising a housing provided with a gases inlet, the gases inlet being in fluid communication with a patient outlet to deliver a gases flow to the patient via an intermediate passageway, and a chamber and a heater, a controller being provided operative to control the apparatus according to a disinfection mode in which the heater heats liquid to produce vapour or steam at or above a target dewpoint temperature, the apparatus being arranged such that the vapour is delivered to the intermediate passageway to disinfect the intermediate passageway with moist heat, the disinfection mode having a predetermined duration, the controller being operative to subsequently control the apparatus such that the vapour at or above the target dewpoint temperature continues to be delivered to the intermediate passageway throughout the predetermined duration of the disinfection mode.

The apparatus may comprise a safety cap provided with a connector arranged to fluidly couple the safety cap to a downstream end of the intermediate passageway, and a duct forming a vapour flow path into the safety cap, the safety cap being adapted to disperse and/or condense vapour received thereby. The safety cap may comprise a condensing surface onto which vapour from the duct condenses and/or a condensate reservoir adapted to receive condensate generated by the safety cap.

According to another aspect, there is provided a respiratory assistance apparatus adapted to deliver a gases flow to a user or patient, the apparatus comprising a housing provided with or configured to receive a chamber and a heater, the chamber comprising at least one port connected to, or arranged to be connected to, at least one intermediate passageway, the apparatus being operative according to a disinfection mode to heat liquid in the chamber to generate vapour or steam at or above a target dewpoint temperature and deliver the vapour from the chamber to the intermediate passageway to disinfect the intermediate passageway with moist heat, the apparatus further comprising a safety cap provided with a connector arranged to connect and/or fluidly couple the safety cap to a downstream end of the intermediate passageway, thereby defining a gases pathway from the chamber to the safety cap, the safety cap being adapted to, in use in the disinfection mode, disperse and/or condense at least a portion of vapour received thereby.

The may comprise a duct defining the gases pathway into the safety cap, the safety cap further comprising a condensing surface onto which vapour from the duct condenses. Additionally or alternatively, the apparatus may comprise a condensate collector adapted to collect at least a portion of the condensate generated by the safety cap.

According to another aspect, there is provided a safety cap for use with the respiratory apparatus of any one of the previous aspects, the safety cap comprising a connector arranged to fluidly couple the safety cap to a downstream end of the intermediate passageway, and a duct forming a vapour flow path into the safety cap, the safety cap being adapted to, in use in a disinfecting mode, disperse and/or condense vapour received thereby.

Preferably, the safety cap comprises a condensing surface onto which vapour from the duct condenses. The condensing surface may have a surface area greater than the cross sectional area of the duct and/or a domed ceiling into which the duct directs the vapour flow path. A skirt may extend generally downwards from a peripheral edge of the ceiling to define an area for holding vapour and/or directing flow of condensate.

The safety cap may be adapted to direct vapour radially outwardly of the connector prior to the vapour impacting on the condensing surface, aiding in dispersion of the vapour and reducing the likelihood of localized hot spots. The duct may be defined by a wall having at least one vapour outlet through which vapour can flow away from a longitudinal axis of the duct. The or each vapour outlet comprises a slit formed in the wall defining the duct. The condensing surface may be connected to the duct via at least one spoke extending between the condensing surface and the duct. A vapour outlet may be provided in the wall of the duct between one or more adjacent pairs of said spokes. The duct may be terminated at an end distal from the intermediate passageway by an end wall.

The safety cap may comprise an identifier. The identifier may comprise a resistor, the resistance of which is detected by the apparatus when the safety cap is mounted on the apparatus.

The safety cap may comprise one or more surfaces having a hydroscopic structure arranged to promote the formation of condensate. Additionally or alternatively, microstructures may be arranged to channel flow of condensate. The safety cap may comprise a condensate collector that defines a reservoir into which condensed vapour is collected. The condensate collector may comprise a substantially annular catch tray extending around the periphery of the connector. The condensate collector may comprise a spout to facilitate pouring of liquid from the condensate reservoir. Further, the condensate reservoir may be arranged to measure a predetermined volume of liquid for use during the disinfecting mode of the respiratory apparatus.

According to another aspect, there is provided a respiratory assistance apparatus adapted to deliver gas to a user or patient, the apparatus comprising a housing provided with or configured to receive a chamber and a heater, the chamber comprising at least one gas port connected to, or arranged to be connected to, at least one intermediate passageway, the apparatus being operative according to a vapour disinfection mode to disinfect the at least one intermediate passageway with moist heat, the apparatus comprising a controller for controlling operation of the apparatus in the disinfection mode, to activate the heater to heat liquid in the chamber to generate vapour at or above a target dewpoint temperature for at least a portion of the duration of the disinfection mode.

In an initialization phase, the controller may be arranged to detect the presence or absence of any one or more of the chamber, an attachment for use with the apparatus in the disinfection mode, and liquid in the chamber, and/or a level of liquid in the chamber. The disinfection mode is automatically activated or is able to be activated following a positive detection of the chamber and/or attachment and/or liquid and/or the predetermined level of liquid.

The apparatus may comprise a compressor in fluid communication with the chamber for urging gases through the chamber to the at least one intermediate passageway, wherein during a warm up phase and/or a main disinfecting phase, the controller is adapted to control the heater to generate vapour and to control the compressor to provide no or only a low level of increased flow. The compressor can be used to control a flow rate of humidified gases flow and the compressor can be controlled to provide no or only a low level of increased flow during a main disinfection phase of the disinfection mode. The low level of flow can be less than about 10 L/min or less than about 2 L or less than 1 L/min.

Prior to termination of the disinfection mode, the controller may be configured to control the compressor to provide a ramped increase in flow so as to dry and/or cool down at least a portion of the apparatus or the at least one intermediate passageway. The compressor can provide a ramped increase to greater than 20 L/min or greater than 40 L/min or greater than 60 L/min. The controller may be configured to switch off the heater and/or the compressor upon detection of any one or more of an absence of liquid in the chamber, a temperature of a portion of the apparatus falling below a predetermined threshold, a temperature detected inside the apparatus falling below a predetermined threshold and elapse of a predetermined time period.

Preferably, the compressor is controlled to slowly discharge any remaining vapour or steam from the chamber near the end of the disinfection mode and then to provide a higher flow rate subsequent thereto so as to provide for accelerated drying and/or cooling. The initial low flow helps to prevent injury since relatively high energy steam or vapour is ejected relatively slowly before the lower energy air stream is forced from the chamber at a higher flow.

The controller may be arranged to generate a signal indicative of whether the disinfection mode was completed successfully and/or log one or more parameters relating to the disinfection mode cycle.

Further aspects of the invention, which should be considered in all its novel aspects, will become apparent from the following description.

BRIEF DESCRIPTION OF THE DRAWINGS

A number of embodiments of the invention will now be described by way of example with reference to the drawings.

DETAILED DESCRIPTION OF THE PREFERRED EMBODIMENT

Figure 1:
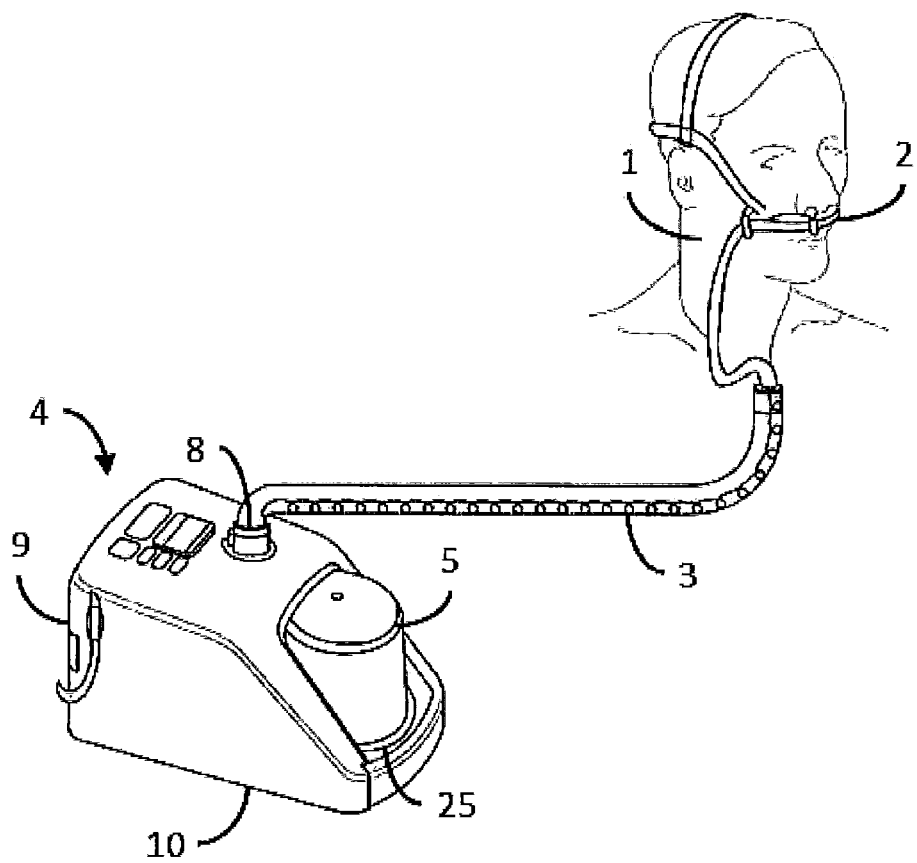
FIG. 1 is a perspective view of a respiratory assistance apparatus in accordance with the invention, in use with an inspiratory tube and patient interface.
Figure 2:
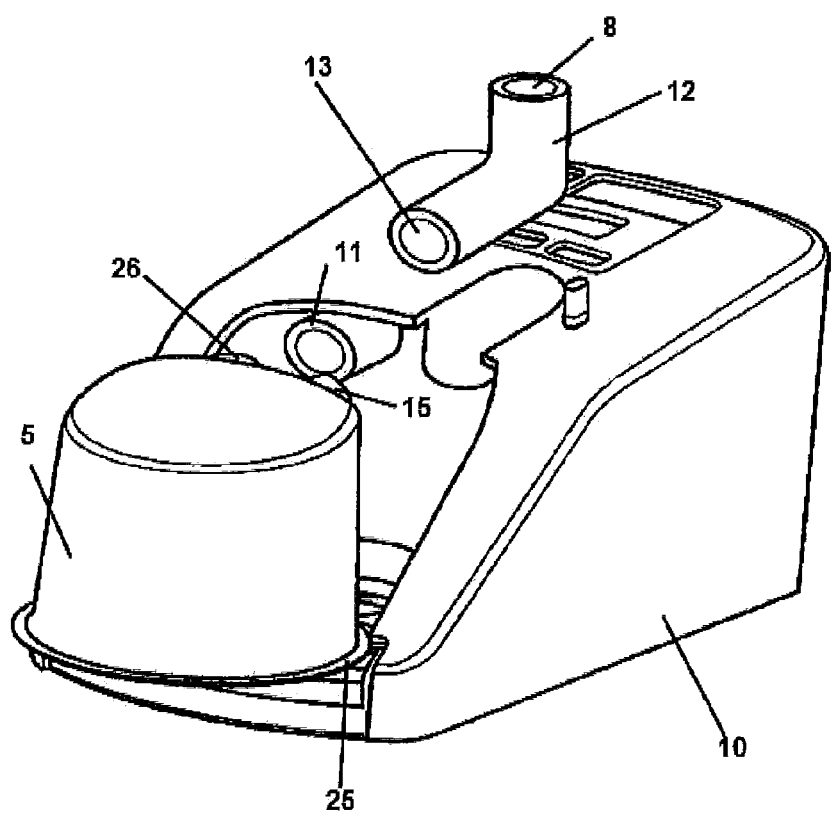
FIG. 2 is a partially exploded perspective view of a respiratory assistance apparatus in accordance with the invention.
Figure 3:
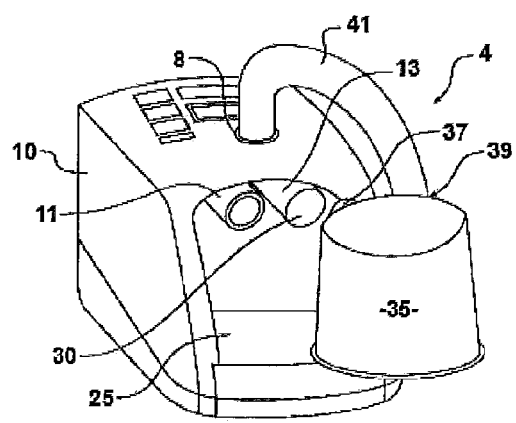
FIG. 3 is a perspective view of a further respiratory assistance apparatus in accordance with the present invention, with the device in a partially disassembled condition.
Figure 4:
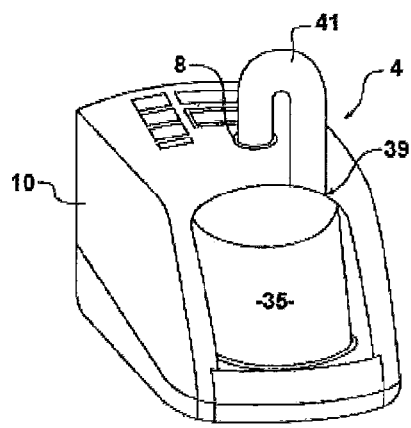
FIG. 4 is a perspective view of the apparatus of FIG. 3 in an assembled condition.
Figure 5:
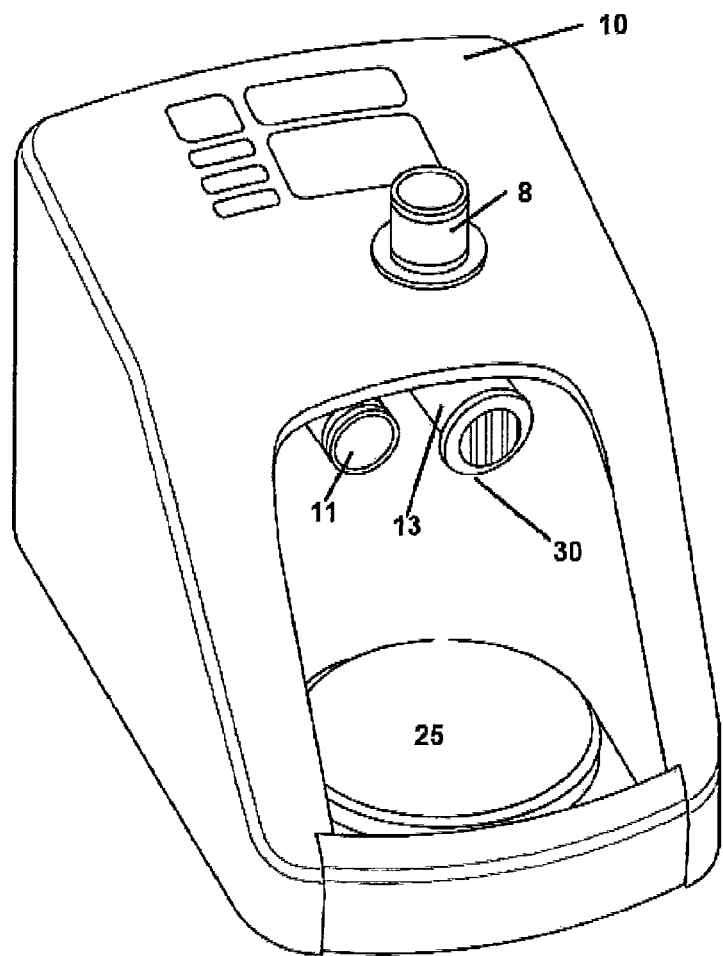
FIG. 5 is a perspective view of the apparatus of FIGS. 1 and 2, including a cap closing a patient outlet.
Figure 6:
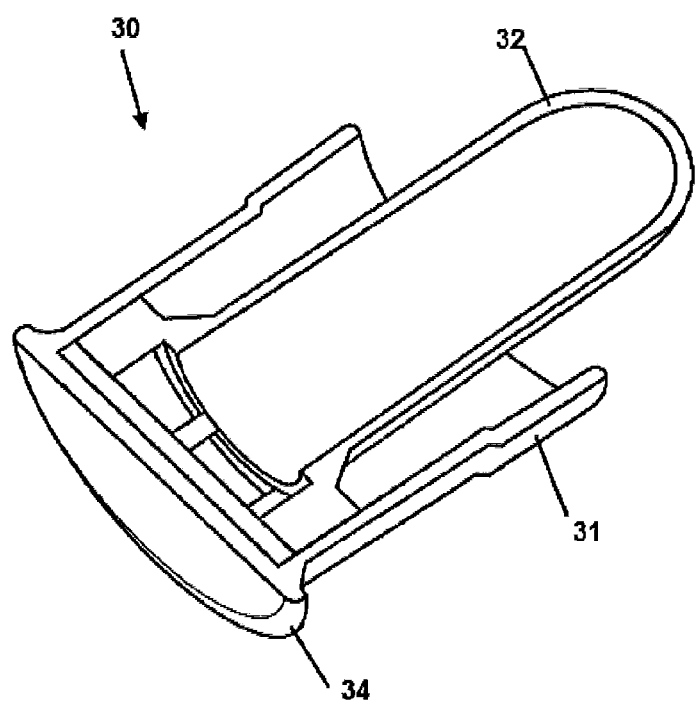
FIG. 6 is a perspective sectional view of a cap for use with an apparatus in accordance with the invention.
Figure 7:
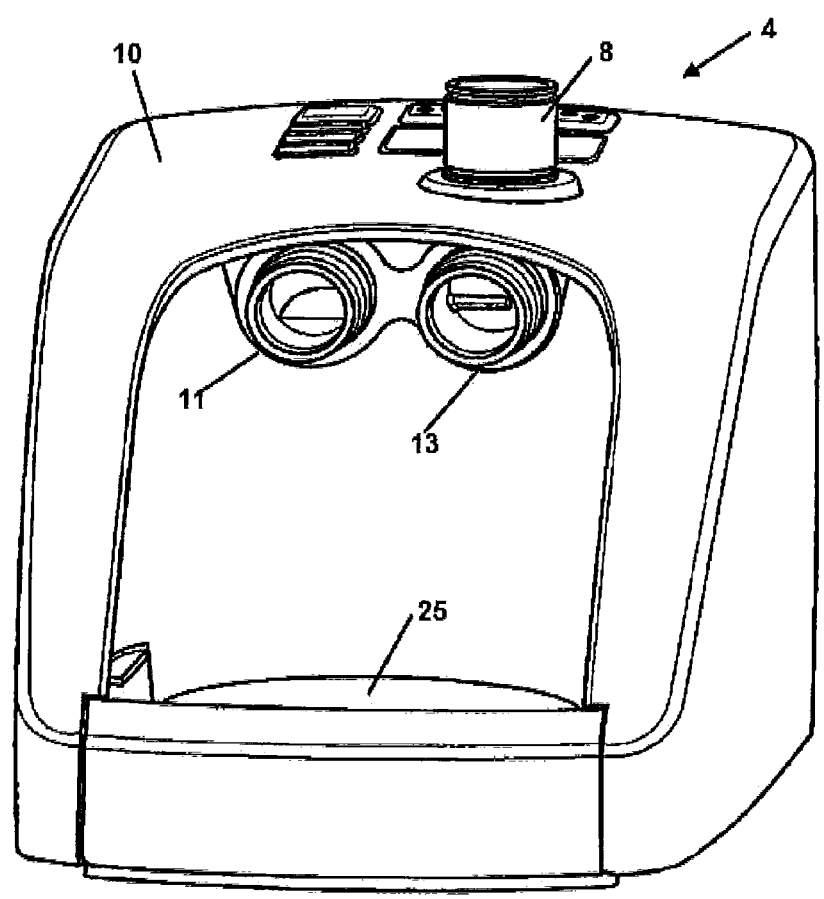
FIG. 7 is a further perspective view of an apparatus in accordance with the present invention.
Figure 8:
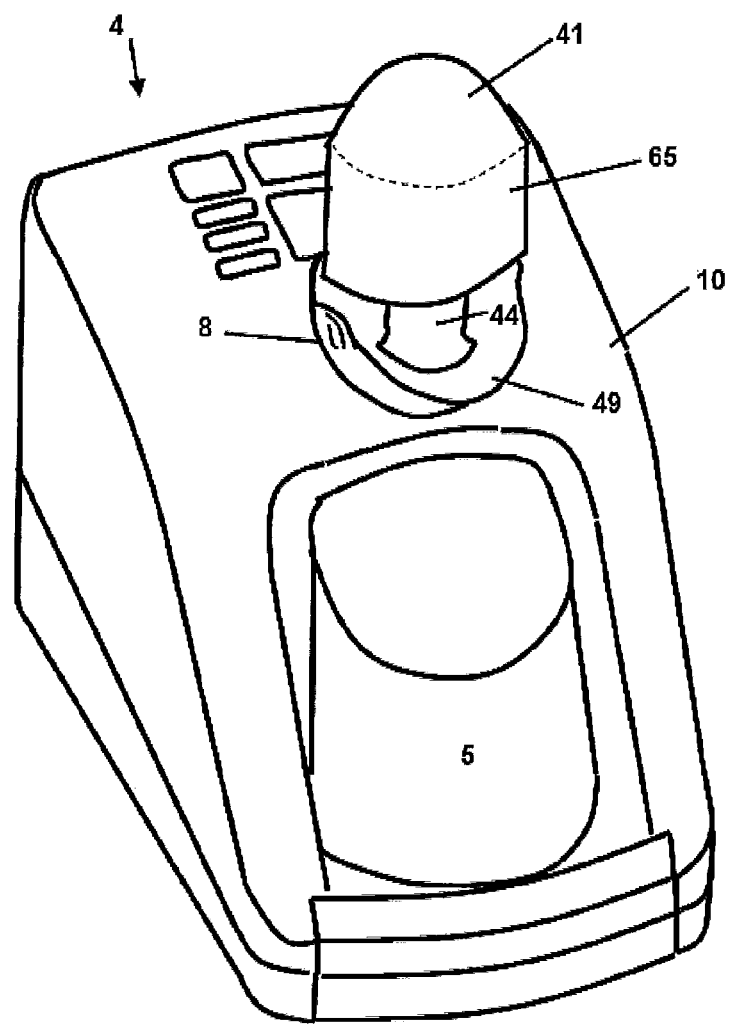
FIG. 8 is a perspective view of a respiratory assistance apparatus in accordance with the invention, including a safety cap.
Figure 9:
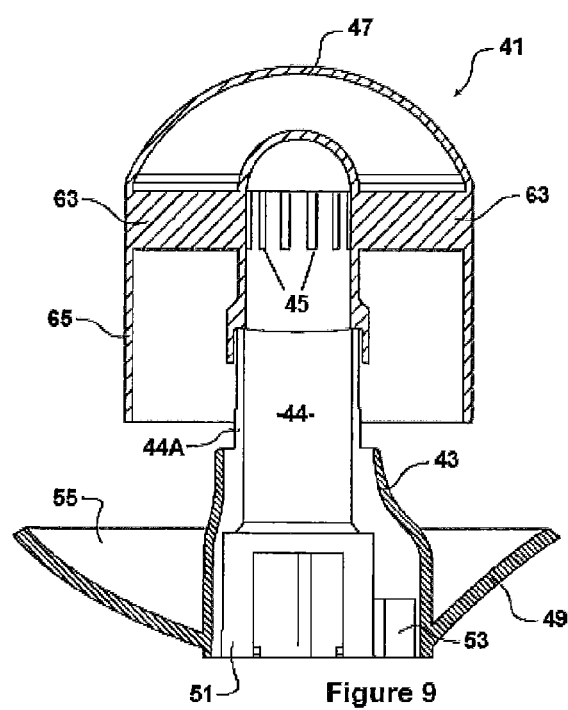
FIG. 9 is a sectional view of the safety cap of FIG. 8.
Figure 10:
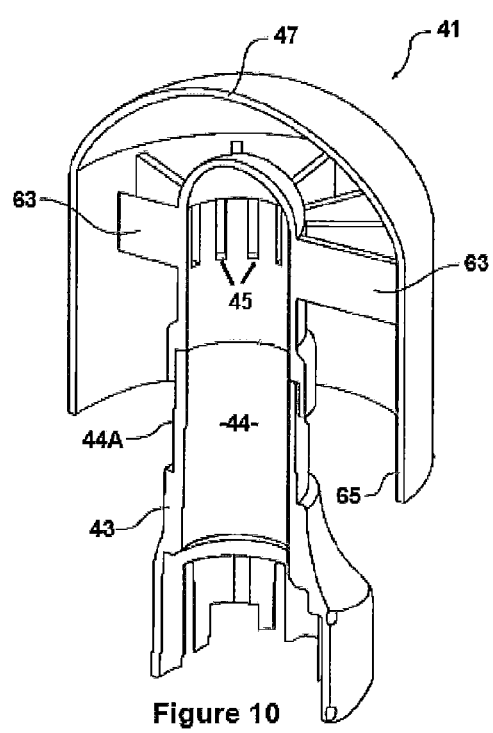
FIG. 10 is a perspective sectional view of the cap of FIG. 9, with a condensate reservoir of the safety cap removed.

Throughout the description like reference numerals will be used to refer to like features in different embodiments.

The present invention provides a respiratory assistance apparatus that provides a convenient, effective and reliable method of disinfecting at least a portion of the apparatus with moist heat during a disinfection mode, which portion may define, at least in part, a transport path for a humidified gases flow generated by the apparatus. According to some embodiments, the at least a portion of the apparatus comprises an internal passageway provided at least partially inside the apparatus. The present invention also provides a method of disinfecting a respiratory assistance apparatus and attachments for use with such method of disinfecting the respiratory assistance apparatus.

A chamber is provided on or at the apparatus in which liquid can be heated to produce vapour or steam, the vapour being delivered to the at least a portion of the apparatus (such as the internal passageway) to disinfect that portion with moist heat. The invention provides for the chamber being the same humidification chamber used to humidify the gases flow prior to delivery to the patient during normal use of the apparatus to provide respiratory assistance. The invention also or alternatively provides for a separate chamber to be used. In this latter example, in the disinfecting mode, the humidification chamber may be removed, and replaced with a disinfecting chamber. The disinfecting chamber may be a reusable, refillable chamber, or may be supplied pre-filled with the required amount of disinfecting liquid and pre-sealed.

The invention provides for the use of water and therefore vapour or steam to disinfect said at least a portion of the apparatus with moist heat. Other liquids, or combinations of liquids, could be used as required.

The invention provides for the source of liquid that is used for disinfection to be a self contained part of the apparatus, namely located on or at the apparatus in use of the disinfection mode.

Referring to the Figures, a respiratory assistance apparatus 4 comprises a housing 10 which may be generally cuboidal and may be arranged to be placed on a table or tray, or mounted on a wall or some other support, as required or preferred.

A supply gases inlet 9 is provided, for example on the rear of the housing, and is in fluid communication with a gases source such as a blower, fan or compressor (not shown), preferably mounted in the housing 10 for delivering a gases flow. There may be ductwork within the housing which connects the gases source with the supply gases inlet 9, and that ductwork may be of a length and path direction selected as required.

The housing 10 is further provided with a supply gases outlet 11, which may project from the front of the housing 10, from which the gases flow exits.

Preferably, adjacent the supply gases outlet 11 is a patient inlet 13 which may also project from the front of the housing 10, which leads to a patient outlet 8 which may project from the top of the housing 10. The patient inlet 13 and the patient outlet 8 are connected by an intermediate passageway, which in this example comprises an elbow 12 that is bent along its length through 90°. The patient inlet 13 and patient outlet 8 may be otherwise positioned depending on the apparatus configuration, with the elbow 12 configured to provide fluid communication between the patient inlet 13 and the patient outlet 8. Thus, the elbow 12 may be of some alternative configuration, including but not limited to straight, curved, or bent in more than one location.

In this example, a humidifier is provided having a chamber 5 comprising a chamber inlet port 26 and a chamber outlet port 15. The ports 26, 15 are provided on the rear of the chamber 5, and sealingly engage with the supply gases outlet 11 and the patient inlet 13, respectively, such that in use the gases flow enters the chamber 5 from the supply gases outlet 11 through the chamber inlet port 26 and exits the chamber 5 to the patient inlet 13 through the chamber outlet port 15.

The chamber 5 may be removably mounted on the housing 10, and in one example, may be slidably mounted on the front of the housing 10 by sliding the chamber 5 towards the rear of the housing 10 until the ports 11, 26 and the ports 13, 15 engage. In another example, the chamber 5 may be permanently mounted on the housing 10.

A heater 6 is provided which in this example comprises a heater plate 25 on the housing 10, below the chamber 5. Other forms of heater are envisaged and these may include a heater element built into the chamber 5 itself or a non-contact heater such as an induction heater for example.

A controller may be provided in the housing 10 which is arranged to control the gases source and the heater. It will be appreciated that by providing appropriate communication means, control may be effected, at least in part, remote from the apparatus.

The apparatus 4 is operative according to at least two modes: a respiratory mode and a disinfection mode.

In the respiratory mode, the gases source is controlled to provide a gases flow to the chamber 5. The gases flow passes into the chamber inlet port 26, across the chamber 5, and out of the chamber outlet port 15. The heater 25 is controlled to heat liquid in the chamber 5 such that the incoming gases flow passes over the liquid and is humidified by vapour generated from the heated liquid. This heated and humidified gases flow exits the chamber 5 via the chamber outlet port 15 and is delivered to a patient 1 via the elbow 12 and the patient outlet 8. While various interfaces are known and may be selected based on operational parameters and user preferences, FIG. 1 shows a particular inspiratory tube 3 having a heating element 7 running therethrough, and coupled at one end to the patient outlet 8 and at the other to a patient interface 2 (shown as a nasal cannula).

In the disinfection mode, the gases source may be switched off, or may be controlled to continue delivering a gases flow into the chamber 5 at the same or a different flow rate. The heater is controlled to heat liquid in the chamber 5 to produce steam or vapour at or above a target dewpoint temperature. The vapour fills the chamber 5 and is delivered into the elbow 12 and through the patient outlet 8. The vapour in the elbow 12 provides the moist heat that serves to disinfect the elbow 12 and the patient outlet 8. The disinfection mode is operative for a predetermined duration in which the heater 25 is controlled such that vapour continues to be generated and supplied to the elbow 12 throughout the duration of the disinfection mode.

The target dewpoint temperature is set sufficiently high that the vapour provides the moist heat necessary to disinfect the elbow 12, at least over the duration of the disinfection mode. The target dewpoint temperature is inversely proportional to the duration of the disinfection mode, at least within a preferred temperature range of 70° C. to 100° C. Thus, a fixed target dewpoint temperature and disinfection mode duration may be predetermined, or may be variable according to a user selection of one of the target dewpoint temperature or the disinfection mode duration. A lookup table may be provided which relates the duration required for a range of target dewpoint temperatures. As an example only, a range of dewpoint temperatures between 70° C. and 90° C. may achieve sufficient disinfection efficacy over a disinfection mode duration of between 15 and 45 minutes, preferably around 30 minutes. As will be appreciated, to ensure sufficient disinfection efficacy, a safety margin may be applied to the dewpoint temperature and/or duration.

In this example, the disinfection mode therefore requires no external components, or modifications to the apparatus 4, instead using the components of the humidifier in a different manner to achieve disinfection. No external disinfection hoses or the like are required, and it is not required to remove the chamber 5 from the housing 10.

Optionally, an end cap 30 is provided which is arranged to be mounted on the end of the elbow 12 at the patient outlet 8.

The cap 30 comprises an engaging formation 31 arranged to engage with the end of the elbow 12 at the patient outlet 8 to mount the cap 30. The cap 30 may further comprise a flow restrictor 32 arranged to restrict flow through the elbow 12 when the cap 30 is so mounted, to provide back pressure in the elbow 12 during the disinfection mode. The cap 30 may further comprise an antibacterial filter. The cap 30 may also comprise an identifier such as a RFID tag, or a resistor which is used by the apparatus 4 to determine if the cap 30 is mounted on the elbow 12.

The apparatus 4 may comprise a chamber sensor operative to generate a signal indicative of whether the chamber 5 is mounted on the apparatus 4. The chamber sensor may be operative to generate a signal indicative of whether a specific chamber or type of chamber is mounted on the apparatus 4. The chamber sensor may comprise the combination of a pressure/flow sensor and a flow restriction on the specific chamber, the flow restriction restricting gases flow through the chamber which can be detected by the pressure/flow sensor.

The apparatus 4 may comprise a patient interface sensor operative to generate a signal indicative of whether a patient interface is connected to the apparatus 4, and to activate the disinfection mode only when the signal is indicative that a patient interface is not connected to the apparatus 4. The patient interface sensor may be operative to detect the presence of the cap 30 on the end of the elbow 12 at the patient outlet 8, and to generate the signal indicative that a patient interface is connected to the apparatus 4, when no cap 30 is detected.

The apparatus 4 may comprise a disinfection mode sensor operative to generate a signal indicative that the apparatus 4 is to operate according to the disinfection mode. The disinfection mode sensor may be operative to generate the signal by detecting at least one of: the cap 30 being mounted on the end of the elbow 12 at the patient outlet 8; the chamber 15 being mounted on the housing 10; and/or a user input.

The apparatus 4 may comprise a chamber liquid level detector operative to generate a signal indicative of a liquid level in the chamber 5. The apparatus 4 may be operative, in dependence upon the liquid level signal detected, to vary at least one of: the flow rate of the gases flow; the target dewpoint temperature of the vapour; and/or the duration of the disinfection mode.

The liquid level detector may indicate when the disinfection liquid has been entirely used, so as to determine whether a sufficient duration and dewpoint temperature combination has been achieved to provide the desired disinfection efficacy.

The apparatus 4 may provide a drying mode, initiated subsequent to the disinfection mode, wherein the elbow 12 and/or other components of the gases flow path are dried. This may be achieved using heat generated by the heater when all of the liquid in the chamber 5 has been entirely used, or via a separate heater element, or via increasing the gases flow rate through the elbow 12, for example. The duration of the drying mode may be predetermined, user controlled, or controlled in dependence on moisture levels detected in the elbow 12.

A drying mode may also be provided to dry the moisture from components of the gases flow path, such as by operating the blower for a sufficient period after the liquid has been completely used, or after the heater plate has been switched off and the remaining liquid cools and its evaporation approaches an equilibrium state.

In another example, another method of disinfecting the elbow 12 is provided. This example uses a separate disinfection chamber 35 which is mounted on the housing 10 for the duration of the disinfection mode. This method can therefore be used on an apparatus not provided with a humidification chamber 5, or otherwise requires removal of the humidification chamber 5 when provided.

In this example, the disinfection chamber 35 is mounted on the housing 10 with the chamber inlet port 37 sealingly connected to the supply gases outlet 11 on the housing 10. A disinfection hose 41 is connected between the chamber outlet port 39 and the end of the elbow 12 at the patient outlet 8. End cap 30 is mounted on the end of the elbow 12 at the patient inlet 13.

During the disinfection mode, the heater heats liquid in the disinfection chamber 35 to produce vapour at or above a target dewpoint temperature. The vapour flows from the disinfection chamber 35, along the disinfection hose 41 and into the end of the elbow 12 at the patient outlet 8. The vapour flows along the elbow 12, disinfecting the elbow 12, and exits via the end cap 30 on the end of the elbow 12 at the patient inlet 13.

The disinfection chamber 35 may be supplied pre-charged with a suitable volume of disinfecting liquid, or may be provided with an injector inlet or the like through which a suitable volume of disinfecting liquid may be introduced into the chamber 35.

Referring additionally to FIGS. 8 to 15, a safety cap 41 is provided for mounting on the end of the elbow 12 at the patient outlet 8 of the apparatus 4 during a disinfection mode. The safety cap 41 is used during a disinfection mode in which the humidifier chamber 5, or the disinfection chamber 35, is mounted on the apparatus 4 to generate vapour that passes through the apparatus 4, through the elbow 12, and exits the apparatus 4 via the patient outlet 8. It will be appreciated that without safety measures, vapour exiting the patient outlet 8 could scald a user or other person near the apparatus 4. Similarly, portions of the apparatus 4 impinged by the vapour could become dangerously warm. Broadly speaking, the safety cap 41 provides a means of mitigating these risks by dispersing the vapour, so that it is not concentrated in a small area, and by condensing the vapour.

The safety cap 41 comprises a connector 43 arranged to connect the safety cap 41 with the patient outlet 8 at one end of the elbow 12 and a duct 44 extending through the connector 43 to form a gases flow path with the patient outlet 8. The vapour duct 44 is provided, at a position distal from the connector 43, with at least one vapour outlet 45 through which vapour exits the duct 44 in a generally radially outward direction but is retained within the safety cap 41. A concave inner roof 47 provides a condensing surface positioned above the end of the duct 44 and above the vapour outlet 45 such that vapour from the vapour outlet 45 rises and contacts the roof 47. The vapour condenses on the roof 47, and the condensate drops from the roof 47 and is collected in a condensate reservoir 49 below.

The risk of vapour directly contacting a user adjacent the apparatus 1 is therefore reduced by virtue of the tortuous path defined by the safety cap 41, and at least a portion of the vapour is safely condensed and collected within condensate reservoir 49 for later disposal.

The safety cap 41 is arranged to provide a vapour flow path that dissipates the heat from the vapour and/or prevents emission of a hazardous stream of vapour, at least during normal operating conditions. In particular, the vapour duct 44 initially directs the vapour upwardly away from the patient outlet 8, along a central axis of the safety cap 41. The end of the duct 44 is closed by domed end wall 61 (as described further below) such that vapour then flows generally radially outwardly through vapour outlet(s) 45, and subsequently upwardly into contact with roof 47.

The vapour duct 44 and vapour outlet 45 prevent vapour from flowing up the duct 44 directly into contact with the roof 47 and creating a hot spot on the roof 47. Directing the vapour radially away from the vapour duct 44 also prevents any condensate from undesirably flowing back down the duct 44 and into the patient outlet 8.

The roof 47 forms a condensing surface which is impacted by the vapour and which has a surface area that is considerably greater than the cross-sectional area of the duct 44, so that heat energy of the vapour is not concentrated on a particular area of the roof 47. The roof 47, together with other components forming the safety cap 41, serves to dissipate heat from the condensing vapour.

In the illustrated example, the safety cap 41 is of multi-piece construction broadly comprising a base piece forming a lower part 44A of duct 44 and connector 43, the condensate reservoir 49 mounted on the base piece around connector 43, and a cap piece comprising an upper part 44B of duct 44 and roof 47. These pieces may be arranged to be connected together in any suitable manner, including using push fit or snap fit type connections. One or more pieces may alternatively be constructed as a single component.

Connector 43 is a tubular connector comprising a duct connector 51 and an optional electrical connector 53. Connector 43 may be of the same or similar structure to a gases tube connector of the type used to connect a gases tube to the apparatus 1 in normal use, i.e., between the apparatus 1 and a patient interface. When pushed onto the apparatus 1, the duct connector 51 receives part of the patient outlet 8 of the apparatus 1 to form a vapour flow path, whilst the electrical connector 53, when provided, forms an electrical connection with the apparatus 1. Resilient clips 54 releasably engage with corresponding formations on the apparatus 1 to secure the connector 43 onto the apparatus 1. Clips 54 can be pressed inwardly to release the connector 43 from the apparatus 1.

The electrical connector 53 includes any power and/or sensor connections as are required between the safety cap 41 and the apparatus 1. The electrical connector 53 may include an identifier to enable the apparatus 1 to recognize that the safety cap 41 is connected to the apparatus 1. Once the safety cap 41 is recognized, the apparatus 1 may automatically begin a disinfection mode for example. The apparatus 1 may be arranged to prevent activation of a disinfection mode until the safety cap 41 has been connected and recognized by the apparatus 1. In one example, the electrical connector 53 may include an identification resistor which is used to detect the presence of the safety cap 41 on the apparatus 1.

Condensate reservoir 49 comprises a substantially annular catch tray extending around connector 43. The catch tray 49 is generally circular or elliptical when viewed from above, and is of larger diameter than roof 47 to minimize spillage of condensate dropping from the roof 47. The catch tray 49 further preferably comprises a spout 55 from which condensate can be poured to empty the tray 49 after vapour disinfection. The catch tray 49 may also be used to measure a predetermined volume of fluid prior to commencement of a disinfection mode. The catch tray 49 may comprise measuring indicia for this purpose, and/or the volume of the catch tray 49 may correspond to the volume of fluid required. Thus the fluid may be measured in the catch tray 49 and then poured into the humidifier chamber 5, or the disinfection chamber 35, using the spout 55. The periphery of the catch tray 49 may comprise one or more tabs or other gripping formations 57 to facilitate gripping of the tray 49 by a user.

The upper cap piece comprises upper duct part 44B which is mounted on, and fluidly connected to, lower duct part 44A. Upper duct part 44B is closed off by domed end wall 61. Below the domed end wall 61 are a plurality of vapour outlets 45 which in this example comprise equi-spaced slits formed in the duct wall. Any number and/or size and/or shape of vapour outlets 45 can be provided as required. The roof 47 is joined to the upper duct part 44B by a plurality of radially outwardly extending spokes 63, a vapour outlet 45 being provided between each pair of spokes 63. Spokes 63 add thermal mass and heat transfer conduits to the safety cap 41 to assist in cooling the vapour by absorbing heat therefrom. The size and/or number of the spokes 63 may be selected accordingly. The periphery of the concave roof 47 leads to a downwardly directed skirt 65 which assists in directing condensate down into the catch tray 49, minimizing spillage. Skirt 65 also prevents or reduces the amount of vapour ejected via the vapour outlets 45 that escapes the cap 41 and is able to contact a user, maintaining safe operation, at least during normal operating conditions.

Figure 11:
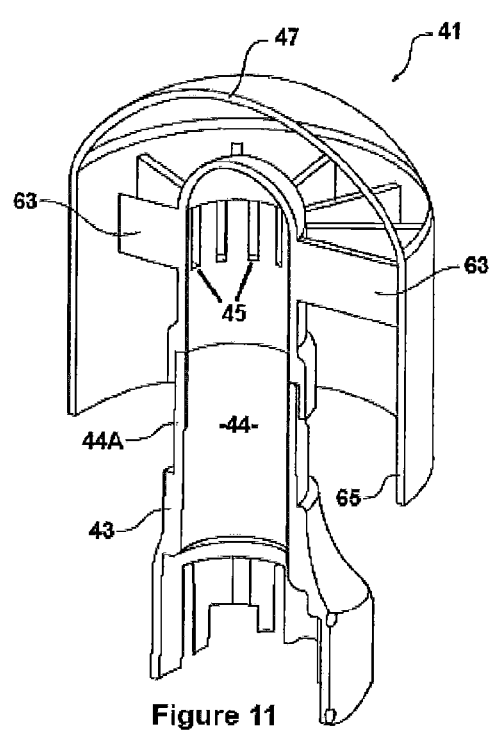
FIG. 11 is a perspective sectional view of the safety cap of FIGS. 9 and 10, with a condensate reservoir of the safety cap removed and an alternative top part.
Figure 12:
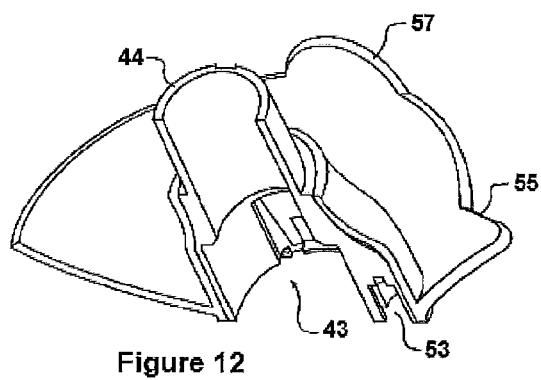
FIG. 12 is a perspective sectional view of a lower part of the safety cap of FIGS. 9 and 10, with an upper part of the safety cap removed.
Figure 13:
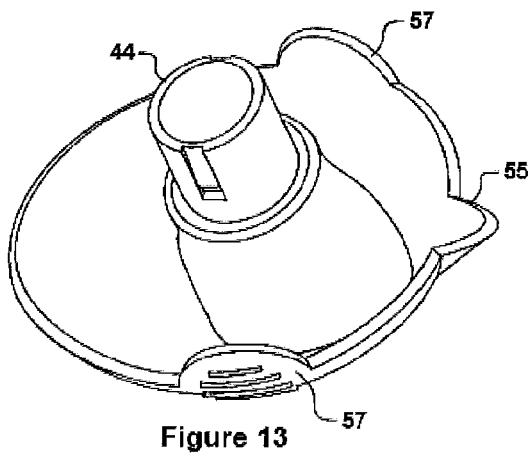
FIG. 13 is a perspective view of the lower part of the safety cap of FIG. 12, with an upper part of the safety cap removed.
Figure 14:
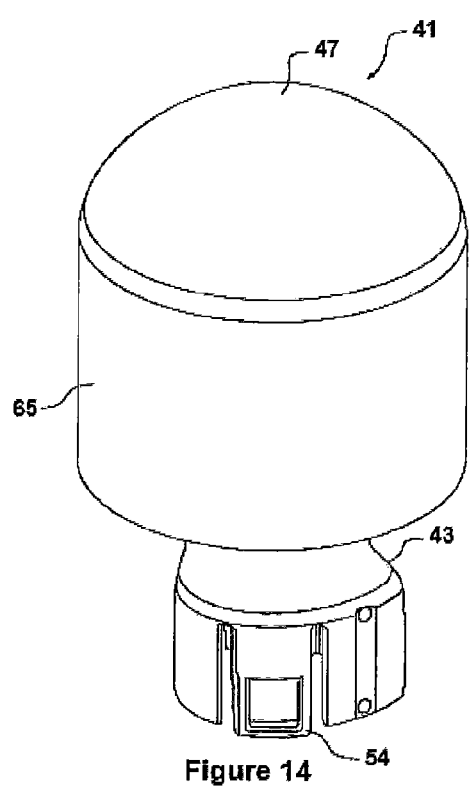
FIG. 14 is a perspective view of the safety cap of FIGS. 9 and 10.
Figure 15:
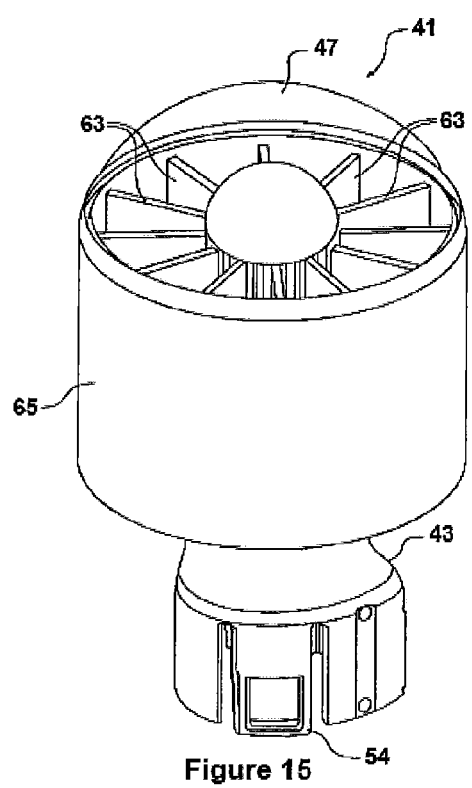
FIG. 15 is a perspective view of the safety cap having the alternative top part of FIG. 11.

With reference to FIGS. 11 and 15 in particular, roof 47 may be transparent or opaque.

Safety cap 41 may optionally further comprise one or more fins or other formations on the exterior of at least part of the cap 41, to prevent a user directly contacting the cap surface and/or to increase heat dissipation from the cap surface, for example roof 47. The inside of the roof 47 may comprise a hydroscopic structure to promote formation of condensation. The roof 47 and/or skirt 65 could comprise microstructures to channel condensate droplet movement down to catch tray 49 as quickly and/or directly as possible.

While the Figures show a particular embodiment of a safety cap according to the invention, various modifications or alternatives are included within the scope of the invention. For example, other structures that serve to disperse the vapour to prevent localized hot spots are also included within the scope of the invention, as are other structures that promote condensation.

With reference to FIGS. 16 to 21, apparatus 1 is arranged to operate according to a disinfection mode. This mode may be activated automatically, for example, when safety cap 41 is mounted on the apparatus 1, or activated when selected by a user. The disinfection mode may be prevented from activating until the apparatus 1 detects the safety cap 41, the cap 30, or some other attachment used in the disinfection mode.

Figure 16:
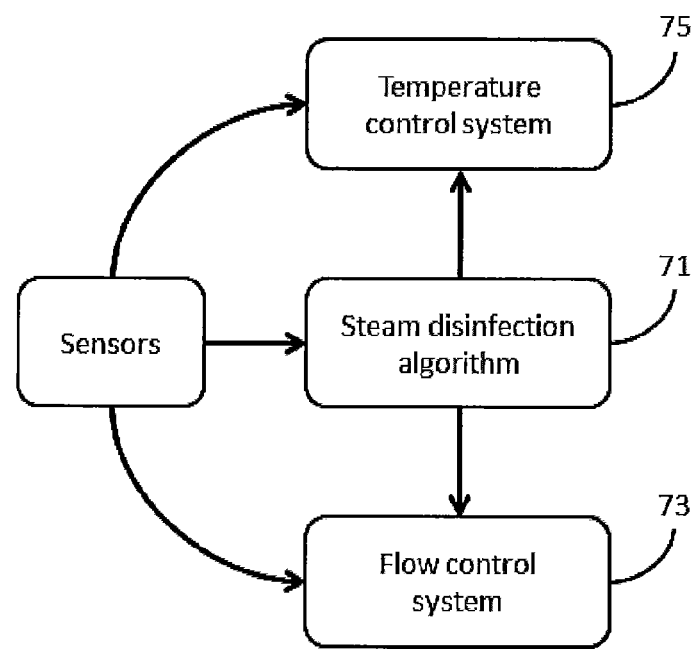
FIG. 16 is an overview of a steam disinfection control system of a respiratory assistance apparatus and method in accordance with the invention.

Referring to FIG. 16, the disinfection mode is controlled via a disinfection controller 71 which receives information from sensors and interacts with a gas flow control system 73 and a gas temperature control system 75. More particularly, flow control system 73 may be operable to control a pressure and/or flow of gas along a gas flow path through the apparatus, at least when in the disinfection mode. It will be appreciated that the same or separate circuitry may be used to control flow when in a respiratory mode. Conversely, the temperature control system 75 may control heating of liquid used in disinfection mode, such as via a heater plate provided in thermal communication with a chamber holding said liquid. According to some embodiments, heating may be provided along the gas flow path to maintain a desired dewpoint temperature and prevent condensation forming. Such heating may comprise a resistance wire heating element provided in a wall defining the gas flow path. Again the same or different circuitry may be employed to similar effect when in a respiratory mode.

Figure 17:
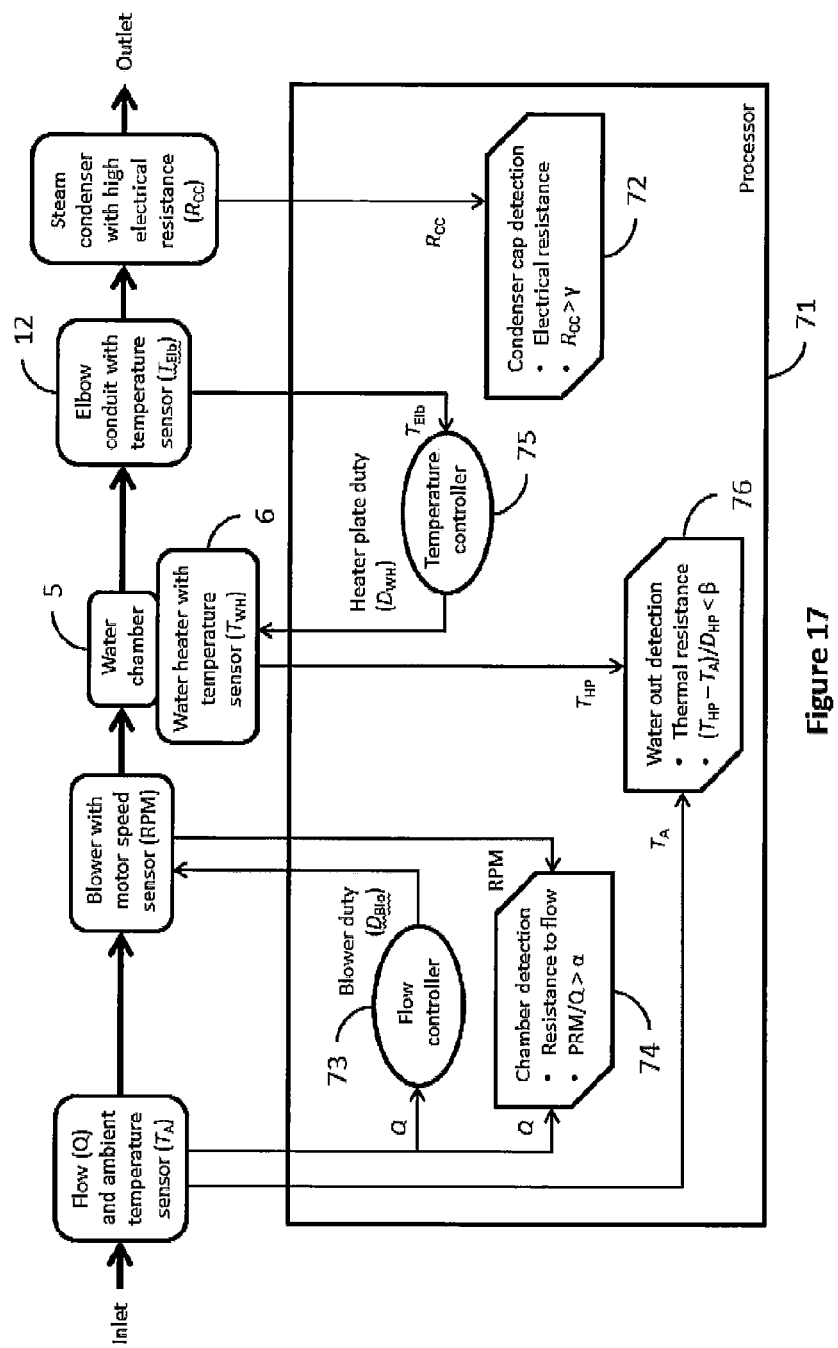
FIG. 17 is a schematic of the steam disinfection control system of FIG. 16.
Figure 21:
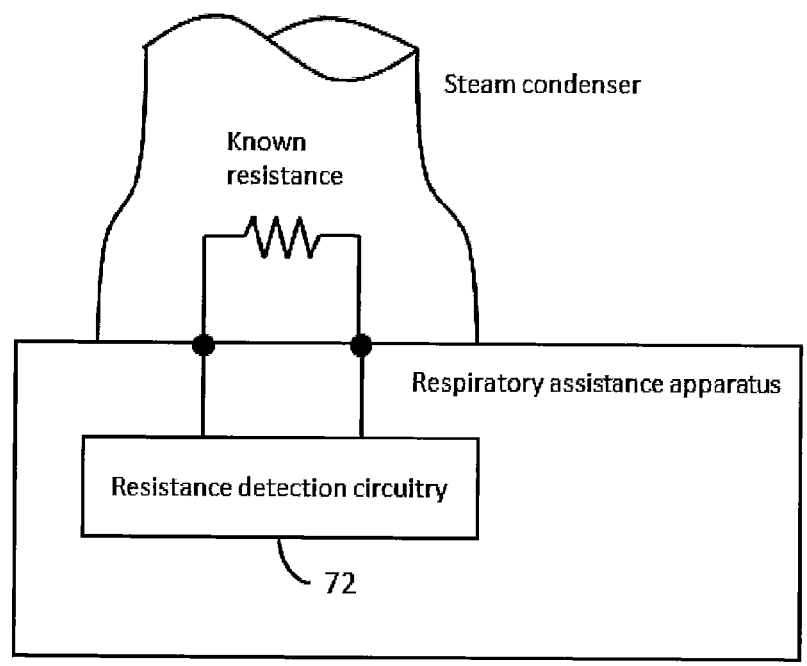
FIG. 21 is a schematic view of a resistance detection circuitry used in connection with the safety cap of FIGS. 8 to 15.

With particular reference to FIGS. 17 and 21, the disinfection controller 71 may be initiated by detecting when the safety cap 41 is connected to the apparatus 1 using an identifier on the safety cap 41. In one example, this detection may be via a measurement of the electrical resistance of a resistor in the electrical connector 53 of cap 41. The detected resistance of the resistor is compared by the disinfection controller 71 to a predetermined resistance value associated with the safety cap 41. For example if the detected resistance exceeds the predetermined resistance value, this signals to the disinfection controller 71 that the safety cap 41 is connected to the apparatus 1. The disinfection controller 71 may then automatically initiate a disinfection mode. The disinfection controller 71 may alternatively use the resistance comparison to allow or prevent an operator from initiating a disinfection mode. As will be appreciated, other forms of detection may be used. For example, apparatus 1 may be operable to detect the presence of an RFID tag form part of the safety cap 41. Optical identification means may alternatively be provided. Alternatively, the detection may be omitted with the disinfection mode being initiated by user input. Such control may additionally or alternatively be used for other embodiments of the invention that do not include the safety cap 41. For example, it may be used to detect the presence of cap 30 or some other attachment used in the disinfection mode.

Flow control system 73 controls the motor speed of the blower, fan or compressor of apparatus 1, at least when in a disinfection mode. The flow control system 73 processes gas flow signals from flow sensors which may be positioned at one or more points along the gas flow path. Additionally or alternatively, flow may be determined based on a signal from a blower motor speed sensor. The apparatus 1 may comprise lookup tables that translate a given motor speed into a flow for determined apparatus configurations (e.g. whether cap 30 or safety cap 41 is connected).

Chamber detection system 74 may be configured to process the outputs from the gas flow sensor and the blower motor speed sensor to determine whether or not the humidifier chamber 5, or the disinfection chamber 35, or safety cap 41, or cap 30, or some other attachment is connected to the apparatus, and whether to initiate the disinfection mode accordingly. Known flow profiles of components may be stored in a memory of the apparatus 1 and used to determine which components are connected based on a comparison with detected flow.

Gas temperature control system 75 controls the heat produced by the heater plate of the humidifier of apparatus 1 using a signal from a gas temperature sensor at or near the patient outlet 8, and/or a signal from a heater temperature sensor at or near the chamber. The gas temperature sensor may be provided in or at the elbow 12, or elsewhere disinfection is required.

Liquid out detection system 76 may be configured to detect when there is no more liquid in humidifier chamber 5 using signals from the ambient temperature sensor and the heater plate temperature sensor.

Figure 18:
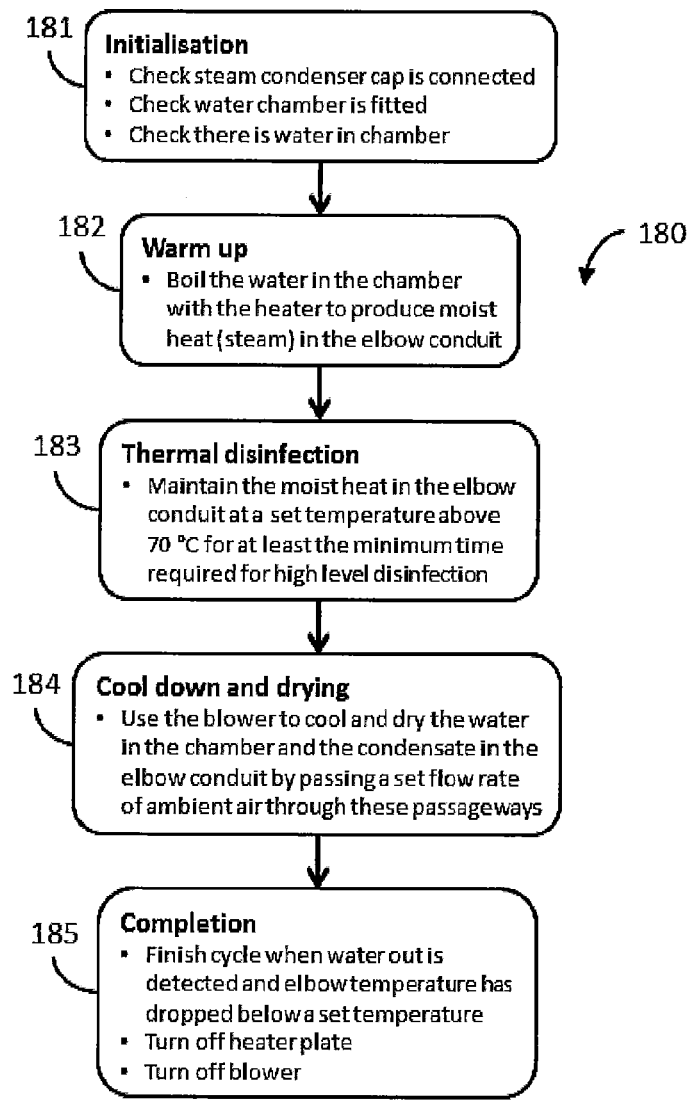
FIG. 18 is a flow diagram showing steps used in the steam disinfection control system of FIGS. 16 and 17.
Figure 19:
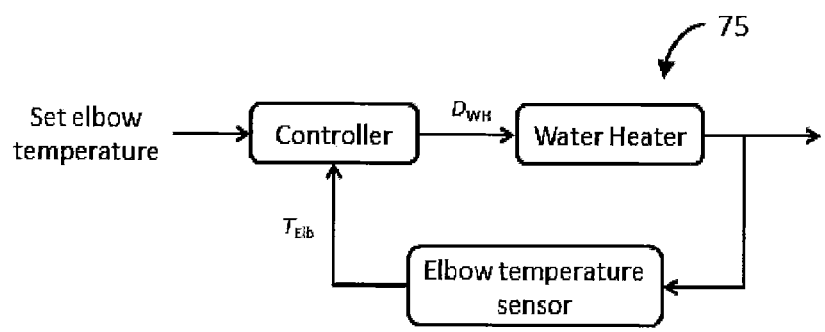
FIG. 19 is a flow diagram of a temperature control system forming part of the steam disinfection control system of FIGS. 16 to 18.
Figure 20:
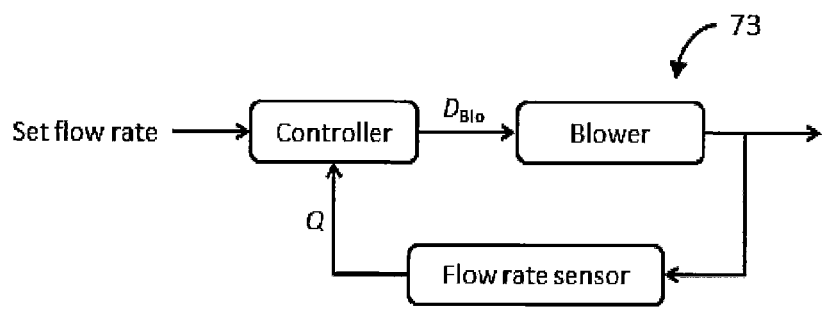
FIG. 20 is a flow diagram of a gases flow control system forming part of the steam disinfection control system of FIGS. 16 to 19.

With reference to FIGS. 18 to 20, a preferred embodiment of an algorithm 181 used by the controller 71 is described that uses the systems 73, 74, 75 and 76, and sensors described above.

The algorithm 180 may begin at step 181 with checks that the apparatus is properly configured for performing the disinfection cycle. For example, controller 71 may detect whether safety cap 41 (or other disinfection mode equipment) and chamber 5 are fitted to apparatus 1. There may also be a check that there is liquid in the chamber 5. The latter may comprise not just detecting a presence or absence of a liquid but a level thereof. While any form of liquid level detector may be used, liquid level may be determined based on the amount of energy used to generate a given change in temperature. For example, current or power supplied to the heater plate may be monitored and a water level inferred based on whether a particular temperature increase is achieved within a predetermined time range. Too rapid a rise in temperature may indicate too little liquid in the chamber. Conversely, a less than expected rise in temperature within a given time period may indicate that too much liquid has been provided. As discussed elsewhere, it is preferable that the disinfection cycle terminates with a drying cycle and too much liquid may prevent this or undesirably lengthen the cycle.

At step 181, the heater plate is controlled to heat the liquid and generate vapour which flows from the chamber, through the elbow 12 and into duct 44 of safety cap 41, via patient outlet 8. Steps 181 and 182 may be combined to some extent where liquid level is determined based on the heater plate duty cycle. Vapour is maintained in the elbow 12 at a temperature above a minimum threshold, such as 70° C. for example, for a time period necessary for a sufficient level of disinfection. During warm up of the apparatus 1 and the disinfection part 183 of the cycle, preferably, flow controller 73 may deactivate the compressor used to enhance flow of gas through the apparatus, with flow being generated due to expansion resulting from vaporization. Alternatively, the flow controller 73 may control the compressor to only generate a relatively small increase in flow. Equipment used for respiratory assistance is configured to generate relatively low temperature humidified gases flows that are suitable for receiving in a patient airway. Higher temperatures are required for disinfection. Reducing or inhibiting flow enhancement provided by the compressor can enable vapour to be generated with the required dewpoint temperature using substantially the same apparatus as that used for providing respiratory assistance and without requiring additional heating. For some compressors used for providing respiratory assistance, low levels of flow may be generated by applying power to a motor of the compressor in pulses, with "ON" pulses in which power is supplied thereto being interspersed by "OFF" cycles when no power is supplied to the motor. Braking may additionally or alternatively be provided.

Completion of the disinfection part 183 of the cycle may be determined based on stored cycle times for a given apparatus configuration and a predetermined or detected level of liquid present in the chamber 5 at the start of the process. Once detected, a cool down and drying phase 184 is initiated that ensures that the walls defining the gas pathway are dry and that they are cooled to a sufficient degree to be comfortably handled by a user and/or used to provide respiratory assistance. This phase 184 preferably comprises increasing the flow enhancement provided by the compressor to dry moisture from the apparatus and then to draw relatively cooler air through the apparatus to cool it. However, rapidly increasing the flow may generate a strong jet of heated humidified gas which may be hazardous. For example, even where safety cap 71 is used, a rapid increase in flow rate may result in a heated vapour stream or cloud forming about the safety cap 71 unless the safety cap 71 is designed to cope with such high flow rates. Thus, according to preferred embodiments, the flow controller 73 gradually ramps up or increases flow to gradually clear the apparatus 1 of high energy vapour.

At step 185, an absence of liquid in chamber 5 is detected and the disinfection mode is terminated provided that the temperature of walls forming the gas pathway have been sufficiently cooled. For example, a temperature at the elbow 12 may be required to have fallen below a predetermined threshold. The heater plate and the compressor are turned off. A signal may be generated to indicate to the operator that the disinfection mode has finished.

The apparatus 1 may be arranged to log one or more parameters of the disinfection process, including but not limited to successful completion of a disinfection cycle, unsuccessful completion of a disinfection cycle, if unsuccessful the reason therefor, a length and/or temperature and/or temperature profile used in the cycle. Such data may be displayed on the apparatus 1 or communicated to remote processing equipment used to collate, analyze or present the data. Thus apparatus 1 may be adapted for wired and/or wireless communication of the data.

From the foregoing it will be seen that apparatus and methods are provided which allow reliable, effective disinfection of an intermediate passageway of a respiratory assistance apparatus, which do not require removal of the intermediate passageway, or any manual intervention or manual cleaning of the passageway. Additionally, apparatus and methods are provided in which disinfecting vapour is generated in situ on the apparatus. Examples are also provided in which the components of the humidifier which are already present on the apparatus, are used in a disinfection mode.

Unless the context clearly requires otherwise, throughout the description, the words "comprise", "comprising", and the like, are to be construed in an inclusive sense as opposed to an exclusive or exhaustive sense, that is to say, in the sense of "including, but not limited to".

Although this invention has been described by way of example and with reference to possible embodiments thereof, it is to be understood that modifications or improvements may be made thereto without departing from the scope of the invention. The invention may also be said broadly to consist in the components, elements and features referred to or indicated in the specification of the application, individually or collectively, in any or all combinations of two or more of said components, elements or features.

Furthermore, where reference has been made to specific components or integers of the invention having known equivalents, then such equivalents are herein incorporated as if individually set forth.

Any discussion of the prior art throughout the specification should in no way be considered as an admission that such prior art is widely known or forms part of common general knowledge in the field.

What is claimed is:

1. A respiratory assistance apparatus adapted to deliver a gases flow to a user or patient, the apparatus comprising:
   a housing comprising a heater, the housing configured to receive a chamber, the chamber comprising at least one chamber port configured to be connected to at least one intermediate passageway,
   a controller programmed to run a disinfection mode,
   wherein the controller is programmed to control the heater to heat a liquid in the chamber to produce vapour at or above a target dewpoint temperature during the disinfection mode, wherein the chamber with the liquid forms a gases flow path with the intermediate passageway during the disinfection mode,
   wherein the controller is programmed to use a combination of some or all of temperature, moisture, and pressure for a predetermined duration of the disinfection mode such that vapour is delivered to the intermediate passageway to disinfect the intermediate passageway with moist heat, the vapour being at or above the target dewpoint temperature and delivered to the intermediate passageway throughout the predetermined duration of the disinfection mode.

2. The apparatus of claim 1, wherein the at least one chamber port comprises a chamber outlet port, wherein the chamber further comprises a chamber inlet port configured to be in fluid communication with a gases source in the housing.

3. The apparatus of claim 1, wherein the controller is programmed to run a non-disinfection mode, the apparatus configured to humidify the gases flow prior to delivery of the gases flow to the user or patient when the apparatus is operating in the non-disinfection mode.

4. The apparatus of claim 1, wherein the chamber comprises an identifier, the apparatus being operative to detect the identifier and thus the presence of the chamber.

5. The apparatus of claim 1, wherein the intermediate passageway comprises an internal passageway located at least partially within the housing, wherein the intermediate passageway is configured to directly or indirectly connect to a gases inlet that allows a gases flow into the housing.

6. The apparatus of claim 1, wherein, during the disinfection mode, a first end of the intermediate passageway is connectable to the at least one chamber port.

7. The apparatus of claim 6, wherein the first end of the intermediate passageway is connectable to the at least one chamber port via a removable disinfection tube which is configured to deliver vapour to the intermediate passageway.

8. The apparatus of claim 7, wherein the disinfection tube comprises heater means.

9. The apparatus of claim 1, wherein the intermediate passageway comprises an elbow having opposed ends linked by an intermediate bent portion.

10. The apparatus of claim 1, wherein the apparatus comprises or is communicatively coupled to at least one sensor operative to generate a signal indicative of flow rate, moisture content, or temperature, wherein the at least one sensor is adapted, in use, to measure a parameter of the gases flow in or proximate to the intermediate passageway.

11. The apparatus of claim 1 further comprising a cap comprising an engaging formation configured to engage with one end of the intermediate passageway.

12. The apparatus of claim 11, wherein the cap comprises (1) a flow restrictor configured to restrict flow of fluid through the intermediate passageway when the cap is engaged with the one end of the intermediate passageway to provide a back pressure in the intermediate passageway during the disinfection mode; (2) a filter; or (3) an identifier detectable by the apparatus to enable the apparatus to recognize that the cap is connected to the apparatus.

13. The apparatus of claim 1, wherein during the disinfection mode, the controller is programmed to control the heater to heat the liquid in the chamber to produce vapour at or above a target dewpoint temperature selected by a clinician or user, wherein the target dewpoint temperature is variable by a user or variable in accordance with a predetermined program.

14. The apparatus of claim 1, wherein the target dewpoint temperature is between 70° C. and 100° C.

15. The apparatus of claim 1, wherein the predetermined duration is between 15 minutes and 45 minutes.

16. The apparatus of claim 1, wherein the controller is programmed to run a drying mode subsequent to the disinfection mode, wherein in the drying mode the intermediate passageway is dried.

17. The apparatus of claim 1, wherein the target dewpoint temperature is about 70° C.

18. The apparatus of claim 1, wherein the target dewpoint temperature is maintained above 70° C.

19. A method of disinfecting at least a part of a respiratory assistance apparatus of claim 1, the respiratory assistance apparatus being adapted to deliver gases flow to a user or patient, the method comprising subjecting said at least a part of the respiratory assistance apparatus to a humidified gases flow at or above a target dewpoint temperature for a predetermined duration of time of a disinfection mode to disinfect the part of the respiratory assistance apparatus with moist heat.

20. The method of claim 19, wherein the apparatus comprises a chamber provided with a port in fluid communication with an intermediate passageway, the method comprising steps of:
heating a liquid in the chamber to produce vapour at or above the target dewpoint temperature;
delivering the vapour through the port to the intermediate passageway; and
continuing to deliver vapour at or above the target dewpoint temperature through the port to the intermediate passageway throughout the predetermined duration of the disinfection mode.

21. A respiratory assistance apparatus adapted to deliver gas to a user or patient, the apparatus comprising:
a housing comprising a heater, the housing configured to receive a chamber, the chamber comprising at least one gas port configured to be connected to at least one intermediate passageway,
a controller programmed to run a vapour disinfection mode,
the controller programmed to use a combination of some or all of temperature, moisture, and pressure for a predetermined duration of the vapour disinfection mode, wherein the chamber with a liquid forms a gases flow path with the intermediate passageway during the vapour disinfection mode,
the controller programmed to control a heater to heat the liquid in the chamber to generate vapour at or above a target dewpoint temperature for at least a portion of the predetermined duration of the vapour disinfection mode.

22. The apparatus of claim 21 wherein, in an initialization phase, the controller is programmed to detect the presence or absence of the chamber, an attachment for use with the apparatus in the vapour disinfection mode, liquid in the chamber, or a level of liquid in the chamber.

23. The apparatus of claim 21 further comprising a compressor in fluid communication with the chamber for urging gases through the chamber to the at least one intermediate passageway, wherein the controller is programmed to control the compressor.

24. The apparatus of claim 23, wherein, prior to termination of the vapour disinfection mode, the controller is programmed to control the compressor to provide a ramped increase in flow.

25. The apparatus of claim 21, wherein the target dewpoint temperature is about 70° C.

26. The apparatus of claim 21, wherein the target dewpoint temperature is maintained above 70° C.

* * * * *